United States Patent

Bertocchio et al.

[11] Patent Number: 5,922,175
[45] Date of Patent: Jul. 13, 1999

[54] PURIFICATION OF CHLOROTETRAFLOUROETHANE BY EXTRACTIVE DISTILLATION

[75] Inventors: Rene Bertocchio, Vourles Par Vernaison; Eric Deslandes, Villeurbanne; Eric Lacroix, Amberieux D'Azergues, all of France

[73] Assignee: ELF Atochem S.A., France

[21] Appl. No.: 09/016,445

[22] Filed: Jan. 30, 1998

[30] Foreign Application Priority Data

Feb. 4, 1997 [FR] France .................................. 97.01219

[51] Int. Cl.⁶ ............................ B01D 3/40; C07C 17/386
[52] U.S. Cl. ................................ 203/57; 203/68; 203/70; 570/178
[58] Field of Search ................................ 203/57, 67, 68, 203/69, 70; 570/177, 178

[56] References Cited

U.S. PATENT DOCUMENTS

| 4,898,645 | 2/1990 | Voigt et al. .......................... 203/67 |
| 4,944,846 | 7/1990 | Manzer et al. ....................... 570/178 |
| 5,129,997 | 7/1992 | Schöttle et al. ..................... 570/178 |
| 5,200,431 | 4/1993 | Dattani et al. ........................ 203/64 |

FOREIGN PATENT DOCUMENTS

| 2141657 | 8/1995 | Canada . |
| 0503771 | 9/1992 | European Pat. Off. . |
| 0 548 744 A1 | 6/1993 | European Pat. Off. . |
| 699 302 | 8/1995 | European Pat. Off. . |
| 6-80592 | 3/1994 | Japan . |
| 9220640 | 11/1992 | WIPO . |
| WO 93/14052 | 7/1993 | WIPO . |
| WO 94/27142 | 11/1994 | WIPO . |
| WO 95/11873 | 5/1995 | WIPO . |
| WO 95/16654 | 6/1995 | WIPO . |
| WO 96/07627 | 3/1996 | WIPO . |

OTHER PUBLICATIONS

French Search Report (Oct. 6, 1997).

*Primary Examiner*—Virginia Manoharan
*Attorney, Agent, or Firm*—Bell, Boyd & Lloyd

[57] ABSTRACT

A process for the purification of 1-chloro-1,2,2,2-tetrafluoroethane (F124) containing 1,2-dichlorotetrafluoroethane (F114) and/or 1,1-dichlorotetrafluoroethane (F114a). The F124 to be purified is subjected to extractive distillation, the extractant being chosen from $C_5$–$C_8$ aliphatic or cycloaliphatic hydrocarbons and $C_4$–$C_8$ perfluoroalkyl halides.

6 Claims, No Drawings

PURIFICATION OF CHLOROTETRAFLOUROETHANE BY EXTRACTIVE DISTILLATION

FIELD OF THE INVENTION

The invention relates to the purification of 1-chloro-1,2,2,2-tetrafluoroethane (F124) containing 1,2-dichlorotetrafluoroethane (F114) and/or 1,1-dichlorotetrafluoroethane (F114a), and its subject-matter is more particularly a purification process in which the two isomeric dichlorotetrafluoroethanes (F114 and F114a) are removed by extractive distillation and easily recovered with a view to their subsequent conversion into products which are harmless to the Earth's atmosphere.

BACKGROUND OF THE INVENTION

F124 is one of the possible substitutes for chlorofluoroalkanes (CFCs), which are affected by the Montreal Protocol and are characterized by an exceptionally long lifetime allowing them to reach high levels of the atmosphere and thus to take part, under the effect of UV radiation, in the destruction of the ozone layer. It is therefore obvious that their substitutes will have to contain only traces of these CFCs.

DESCRIPTION OF THE INVENTION

F124 is generally obtained by fluorination of perchloroethylene with HF in the presence of catalysts which result in more or less considerable formation of dichlorotetrafluoroethanes by dehydrohalogenation/halogenation of the fluoro intermediates.

F124 can also be obtained (less easily) by hydrogenolysis of F114a itself and, in this case, the residual presence of dichlorotetrafluoroethanes is inherent in the process. In all cases the F124 can contain a few per cent of F114 and/or of F114a.

F124 has a low ODP (Ozone Depletion Power): 0.02, as well as an HGWP (Halocarbon Global Warming Potential) lower than 0.1. It can therefore be employed in combination with chlorodifluoromethane (F22), 1-chloro-1-difluoroethane (F142b) or 1,1-difluoroethane (F152a) for the preparation of mixtures of quasi-azeotropic nature, like the refrigerants R409 A and B or 401 A, B or C, intended to replace CFCs like R12 or R500 in the refrigeration industry. It is obvious in this case that an F124 containing as little F114 as possible is wanted, since this latter compound is affected by the regulations which apply to CFCs.

F124 can also be used as synthesis intermediate for the preparation of pentafluoroethane (F125). In this case, during the fluorination of F124 to F125 the two isomeric dichlorotetrafluoroethanes give rise, by fluorination, to the formation of another CFC, chloropentafluoroethane (F115) which is particularly difficult to remove from F125.

The separation of the dichlorotetrafluoroethanes and of F124 can be done by distillation but, in view of the proximity of the boiling points (−12° C. in the case of F124 and 3 and 3.6° C. in the cases of F114 and F114a respectively), satisfactory separation to the range of a hundred ppm of residual dichlorotetrafluoroethanes would require large-sized columns and hence a high capital cost. Although such a process has been recommended in Patent Application WO 95/16654, to obtain an F124 intended to be fluorinated to F125 and containing not more than 2% of F14 and/or of F114a, it is worthwhile to investigate a more effective means of separation and purification in order to remove as much of the dichlorotetrafluoroethanes as possible from the F124.

With the exception of Patent Application WO 95/11873, directed at the removal of F124a ($CF_2ClCF_2H$) from F124 by selective fluorination, all the other publications on purification (WO 93/14052, EP 548 744, JP 06/80592) relate to the removal of olefins from F124 by, respectively, hydrogenation, fluorination with elemental fluorine and adsorption on active charcoal in the presence of oxygen.

Extractive distillation, the principle of which is based on the alteration of the relative volatility of two compounds by addition of a third substance, is in general the technique most widely employed to help to overcome the difficulties of separation by distillation in the absence of advantageous azeotropic compositions. In an extractive distillation process the separation of the constituents of a binary mixture is performed with the aid of a so-called extraction column comprising, successively, from the boiler to the head, three sections, one for exhaustion, the second for absorption and the third for recovery.

The binary mixture to be fractionated is injected at the top of the exhaustion section, whereas the third substance acting as the selective solvent is introduced at the top of the absorption section, so as to travel in the liquid state from its point of introduction to the boiler.

The third, so-called recovery, section, is used to separate by distillation the least absorbed constituent from the traces of solvent entrained under the effect of its nonzero vapour pressure.

This technique has been applied, for example, to the purification of 1,1,1,2,-tetrafluoroethane (F134a) which forms the subject-matter of U.S. Pat. No. 5,200,431. The extractant employed is a chlorinated solvent or an aliphatic hydrocarbon which allows the removal, from F134a, of saturated or unsaturated compounds such as 1,1,2,2-tetrafluoroethane (F134), 1-chloro-2,2-difluoroethylene (F1122), F124, F114 and 1-chloro-2,2,2-trifluoroethane (F133a).

It has now been found that the removal of F114 and/or of F114a from F124 can be easily produced by extractive distillation with the aid of a polar or weakly polar solvents such as hydrocarbons or perfluoroalkyl halides.

The subject-matter of the present invention is therefore a process for purification of a 1-chloro- 1,2,2,2-tetrafluoroethane containing dichlorotetrafluoroethane (F114 and/or F114a) by extractive distillation, characterized in that a $C_5$–$C_8$ aliphatic or cycloaliphatic hydrocarbon or a $C_4$–$C_8$ perfluoroalkyl halide is employed as extractant.

The aliphatic hydrocarbon may be a linear or branched alkane or alkene, such as n-pentane, n-hexane, isohexane and 1-hexene.

Cyclohexane may be mentioned more particularly as an example of cycloaliphatic hydrocarbons.

Perfluoroalkyl halide is intended to mean a compound of formula RfX, in which Rf denotes a linear or branched perfluoro radical $C_nF_{2n+1}$ containing 4 to 8 carbon atoms and X denotes a chlorine, bromine or iodine atom. Among these products it is preferred to employ compounds containing six carbon atoms, in which X is a chlorine atom or a bromine atom.

These compounds RfX can be obtained by various methods described in the literature. The most common method for the preparation of perfluoroalkyl iodides is the telomerization of tetrafluoroethylene with pentafluoroethyl iodide. The other halides (X=Cl or Br) are generally prepared by thermal chlorination or bromination of the iodides.

The process according to the invention can be implemented according to the well-known principles of extractive distillation. The operation is performed in an extractive distillation column in which the F124-F114 and/or F114a mixture to be separated is injected at a point situated at the top of the exhaustion section. The extractant, namely the perfluoroalkyl halide or the hydrocarbon, is introduced into the column at a point situated at the top of the absorption section; it travels in the liquid state from its point of introduction to the boiler.

The diameter and the number of stages of extractive distillation column, the reflux ratio and the optimum temperatures and pressures can be easily calculated by a person skilled in the art from the property data on the individual constituents and on their mixtures (relative volatilities, vapour pressures and physical constants).

The suitability of a solvent to be used for the purification of an F124 by extractive distillation is assessed from its selectivity (S), defined as the ratio of the solubilities of F114 or F114a ($s_{114}$ or $s_{114a}$) and of E124 ($s_{124}$) in the solvent at a partial pressure of 1.4 bars absolute and at a temperature of 25° C.:

$$S = s_{114}/s_{124}.$$

To determine these solubilities a stainless steel autoclave with a capacity of 471 ml is employed, into which a known quantity of solvent is introduced by trapping or direct pouring. After the air has been removed, the whole is heated from the temperature of liquid nitrogen to the ambient temperature and then placed in a vessel thermostated at 25° C. The quantities of F114 (or F114a) or of F124 which are necessary to obtain a change in pressure of close to 1.4 bars are then introduced through a valve. After equilibration, the total pressure and the weights of F114 (or F114a) or of F124 introduced are noted and a sample of the liquid phase and a sample of the gas phase are taken using appropriate devices and then analysed by gas chromatography.

The molar composition of the gas phase allows the partial pressure of F114 (or F114a) or that of F124 to be calculated. The solubility of F114 (or F114a) or that of F124 per litre of solvent in liquid phase is calculated from the molar composition of the liquid phase using the relation:

$$s = 1000 \times x \times M \times d'/x' \times M'$$

in which x and x' denote, respectively, the molar fractions of F114 (or F114a) or of F124 and of solvent which are present in the liquid phase (x+x'=1), M and M' denote, respectively, the molecular mass of F114 (or F114a) or of F124 and that of the solvent, and d' is the density of the solvent in liquid phase at 25° C.

EXAMPLES

The following examples, in which the pressures shown are in bars absolute, illustrate the invention without limiting it.

EXAMPLE 1

123.8 g of n-perfluorohexyl chloride $C_6F_{13}Cl$ are placed in the measurement cell (stainless steel autoclave with a volume of 471 ml, fitted with a magnetic stirring device) and the whole is cooled to liquid nitrogen temperature. The system is next purged of all traces of air and returned to the ambient temperature and then 92 g of dichlorotetrafluoroethane F114 containing, according to analysis, 10% of asymmetric isomer (F114a) are introduced with a suitable device. When the pressure has reached its equilibrium value at 1.45 bars a sample of liquid phase and then a sample of gas phase are taken; the sample of liquid phase is drawn off by transfer under pressure into a 650-$\mu$l microtrap and then vaporized entirely into a volume of 570 ml, so as to allow it to be introduced in gaseous form into the chromatograph. The findings are:

|  | molar % | |
|---|---|---|
|  | Gas phase | Liquid phase |
| F114/F114a | 96.55% | 58% |
| $C_6F_{13}Cl$ | 3.45% | 42% |

These results give a solubility ($s_{114}$) of 1132.4 g of F114 per litre of $C_6F_{13}Cl$ at a partial pressure of 1.4 bars absolute and at 25° C.

The measurement is repeated with 124.1 g of $C_6F_{13}Cl$ and 25.2 g of F124. The pressure equilibrates at 1.475 bars and the composition of the gas and liquid phases is established as follows:

|  | molar % | |
|---|---|---|
|  | Gas phase | Liquid phase |
| F124 | 94.8% | 36% |
| $C_6F_{13}Cl$ | 5.2% | 70% | i.e. a solubility $s_{124}$ of 280.5 g of F124 per litre of $C_6F_{13}Cl$ at a partial pressure of 1.4 bars absolute of F124 and at a temperature of 25° C.

The selectivity of $C_6F_{13}Cl$ for the F114/F124 separation is therefore equal to 4.04.

EXAMPLE 2

The procedure is as in Example 1, $C_6F_{13}Cl$ being replaced with cyclohexane, 47.5 g of which were placed in the measurement cell. After purging at low temperature 128.2 g of F114 were introduced and the pressure was allowed to stabilize at 1.5 bars at 25° C. Analysis of the gas and liquid phases gave the following compositions:

|  | molar % | |
|---|---|---|
|  | Gas phase | Liquid phase |
| F114/F114a | 94.9% | 56.6% |
| Cyclohexane | 5.1% | 43.4% | i.e. a solubility $s_{114}$ of 2017.6 g/l of cyclohexane at 25° C. and at a partial pressure of 1.4 bars absolute of F114.

The cell was emptied and the same measurement was performed, the F114 being replaced with F124. With 46.9 g of cyclohexane and 13.7 g of F124 an equilibrium pressure of 1.5 bars was reached. In these conditions the composition of the gas and liquid phases is as follows:

|  | molar % | |
|---|---|---|
|  | Gas phase | Liquid phase |
| F124 | 92% | 12.2% |
| Cyclohexane | 8% | 87.8% | i.e. a solubility $s_{124}$ of 177 g of F124 per litre of cyclohexane at 25° C. at a partial pressure of 1.4 bars absolute of F124. The selectivity $S = s_{114}/s_{124}$ is therefore 11.4.

EXAMPLE 3

The preceding example was repeated with pure F114a replacing the F114 (which contained 10% of asymmetric isomer). Starting with 115.2 g of F114a and 48.5 g of cyclohexane an equilibrium pressure of 1.5 bars was obtained and a gas phase and a liquid phase exhibiting the following compositions:

|  | molar % | |
|---|---|---|
|  | Gas phase | Liquid phase |
| F114a | 94.9% | 52.4% |
| Cyclohexane | 5.1% | 47.6% | i.e. a solubility $s_{114}$, of 1708 g/l and a selectivity S of F114a relative to F124 of 9.6 (lower than that of the symmetric F114).

EXAMPLES 4 TO 6

The measurements described in the preceding examples were repeated, replacing the cyclohexane successively with n-hexane (b. 69° C.), 2-methylpentane or isohexane (b. 59° C.) and 1-hexene (b. 63.3° C.). The experimental conditions and the results are reported in the table below:

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

| | F114/F114a | | | | F124 | | | | |
|---|---|---|---|---|---|---|---|---|---|
| Solvent | Wt of F114 (g) | Wt of solvent (g) | Equil. P (bar abs) | $S_{114}$ (g/l at 25° C. and 1.4 bar) | Wt of F124 (g) | Wt of solvent (g) | Equil. P (bar abs) | $S_{124}$ (g/l at 25° C. and 1.4 bar) | Selectivity S |
| n-hexane | 108.8 | 40.8 | 1.5 | 1750 | 16.9 | 43.6 | 1.55 | 223.5 | 7.83 |
| iso-hexane | 150.5 | 43 | 1.65 | 2110 | 20.3 | 43.4 | 1.625 | 263.7 | 8 |
| 1-hexene | 162.5 | 42.1 | 1.65 | 2304 | 30 | 46.5 | 1.625 | 375.7 | 6.13 |

We claims:

1. Process comprising purification of 1-chloro-1,2,2,2-tetrafluoroethane (F124) containing 1,2-dichlorotetrafluoroethane (F114) and/or 1,1-dichlorotetrafluoroethane (F114a) by extractive distillation, with $C_5$–$C_8$ aliphatic or cycloaliphatic hydrocarbon or a $C_4$–$C_8$ perfluoroalkyl halide as an extractant.

2. Process according to claim 1, wherein the aliphatic hydrocarbon is a linear or branched alkane or alkene.

3. Process according to claim 1, wherein the cycloaliphatic hydrocarbon is cyclohexane.

4. Process according to claim 1, wherein a perfluoroalkyl halide RfX is employed, in which Rf denotes a linear or branched radical $C_nF_{2n+1}$ containing from 4 to 8 carbon atoms and X is a chlorine, bromine or iodine atom.

5. Process according to claim 4, wherein the halide contains 6 carbon atoms and X is a chlorine or bromine atom.

6. Process according to claim 5, wherein the halide is n-perfluorohexyl chloride.

* * * * *